United States Patent
Malinin

(10) Patent No.: US 8,791,071 B1
(45) Date of Patent: Jul. 29, 2014

(54) CARTILAGE MATERIAL

(71) Applicant: Theodore I. Malinin, Key Biscayne, FL (US)

(72) Inventor: Theodore I. Malinin, Key Biscayne, FL (US)

(73) Assignee: Vivex Biomedical, Inc., Marietta, GA (US)

( * ) Notice: Subject to any disclaimer, the term of this patent is extended or adjusted under 35 U.S.C. 154(b) by 0 days.

(21) Appl. No.: 14/246,588

(22) Filed: Apr. 7, 2014

Related U.S. Application Data

(60) Division of application No. 13/966,676, filed on Aug. 14, 2013, which is a continuation of application No. 13/006,949, filed on Jan. 14, 2011, which is a division of application No. 11/746,877, filed on May 10, 2007, now abandoned.

(51) Int. Cl.
- *A61K 38/00* (2006.01)
- *A61P 19/00* (2006.01)
- *A61L 27/36* (2006.01)

(52) U.S. Cl.
CPC ......... *A61L 27/3612* (2013.01); *A61L 2430/06* (2013.01)
USPC ....................................... 514/17.1

(58) Field of Classification Search
None
See application file for complete search history.

(56) References Cited

U.S. PATENT DOCUMENTS

| | | |
|---|---|---|
| 4,440,750 A | 4/1984 | Glowacki et al. |
| 4,472,840 A | 9/1984 | Jefferies |
| 4,824,939 A | 4/1989 | Simoson |
| 4,932,973 A | 6/1990 | Gendler |
| 4,994,084 A | 2/1991 | Brennan |
| 5,053,049 A | 10/1991 | Campbell |
| 5,073,373 A | 12/1991 | O'Leary et al. |
| 5,290,558 A | 3/1994 | O'Leary et al. |
| 5,306,311 A | 4/1994 | Stone et al. |
| 5,405,390 A | 4/1995 | O'Leary et al. |
| 5,507,813 A | 4/1996 | Dowd et al. |
| 5,510,396 A | 4/1996 | Prewett et al. |
| 5,964,805 A | 10/1999 | Stone |
| 5,968,556 A | 10/1999 | Atala et al. |
| 6,189,537 B1 | 2/2001 | Wolfinbarger, Jr. |
| 7,067,123 B2 | 6/2006 | Gomes et al. |
| 7,335,381 B2 | 2/2008 | Malinin et al. |
| 2003/0143258 A1 | 7/2003 | Knaack et al. |
| 2004/0219182 A1 | 11/2004 | Gomes et al. |
| 2004/0230303 A1 | 11/2004 | Gomes et al. |
| 2005/0020500 A1 | 1/2005 | Shen et al. |
| 2005/0152987 A1 | 7/2005 | Malinin et al. |
| 2005/0196460 A1 | 9/2005 | Malinin |
| 2007/0098759 A1 | 5/2007 | Malinin |
| 2008/0279825 A1 | 11/2008 | Malinin |

FOREIGN PATENT DOCUMENTS

WO   2004096983   11/2004

OTHER PUBLICATIONS

Burkhardt, J.E, et al; "Effects of Difloxacin on the Metabolism of Glycosaminoglycans and Collagen in Organ Cultures of Articular Cartilage"; Fundamental and Applied Toxicology vol. 20 issue Feb. 2, 1993. p. 257-263.

Colnot et al; "Mechanisms of action of demineralized bone matrix in the repair of cortical bone defects"; Clin Orthop Relat Res. Jun. 2005;(435):69-78.

Cook et al; "Repair of articular cartilage defects with osteogenic protein-1 (BMP-7) in dogs"; J Bone Joint Surg Am. 2003;85-A Suppl 3:116-23.

Crites, B.M.; "Autologous chondrocyte transplantation"; Current Opinion in Orthopaedics Jan. 2004; 15(1):45-48.

Jeffrey et al; "Imaging Hyaline Cartilage"; The British Journal of Radiology, 76 (2003), 777-787 E 2003.

Johnson, L.L.; "Arthroscopic abrasion arthroplasty: a review"; Clin Orthop Relat Res. Oct. 2001;(391 Suppl): S306-17.

Lavernia et al; "Bone and tissue allograft use by orthopaedic surgeons"; J Arthroplasty. Jun. 2004;19(4):430-5.

Lindahl et al; "Cartilage repair with chondrocytes: clinical and cellular aspects"; Novartis Found Symp. 2003;249; discussion 175-185, 234-241, 249.

Vangsness Jr. et al; "Restoring articular cartilage in the knee"; Am J Orthop (Belle Mead NJ). Feb. 2004;33(2 Suppl):29-34.

Lindahl et al; "Cartilage repair with chondrocytes: clinical and cellular aspects"; Natl. Library of Med.; Entrez PubMed Abstract (2003).

Malinin et al; "Importance of particle size on healing of bone allografts"; Proc AAOS, 5, 633 (2004).

Poole, A.R.; "What Type of Cartilage Repair Are We Attempting to Attain?" Scientific Article, The Journal of Bone & Joint Surgery. 2003; 85:40-44).

Pottenger et al; "Influence of cartilage particle size and proteoglycan aggregation on immobilization of proteoglycans"; J Biol Chem. Oct. 10, 1982;257(19):11479-85.

Temenoff et al; "Review: tissue engineering for regeneration of articular cartilage"; Biomaterials. Mar. 2000;21 (5):431-40.

Urist et al; "A chemosterilized antigen-extracted autodigested alloimplant for bone banks"; Arch Surg. Apr. 1975;110 (4):416-28.

*Primary Examiner* — Thomas Heard

(74) *Attorney, Agent, or Firm* — David L King

(57) ABSTRACT

Cartilage materials such as cartilage fluff and a cartilage composition comprising a particulate material are disclosed. These are suitable for stimulating chondrogenesis and/or producing cartilage regeneration. Also disclosed are processes for their preparation. Methods for regenerating articular cartilage are also disclosed, which involve, for example, placing the cartilage fluff or cartilage composition into a cartilage defect.

6 Claims, No Drawings

CARTILAGE MATERIAL

RELATED APPLICATIONS

This application is a division of U.S. application Ser. No. 13/966,676 filed on Aug. 14, 2013 entitled "Cartilage Material" which is a continuation of U.S. application Ser. No. 13/006,949 filed on Jan. 14, 2011 entitled "Cartilage Material" which is a division of U.S. application Ser. No. 11/746,877 filed on May 10, 2007.

BACKGROUND OF THE INVENTION

Cartilage, particularly articular cartilage, of higher animals, including man, has a limited potential for repair. Following injuries to articular cartilage, the cartilage generally does not repair itself because of its limited capacity for regeneration. The ability to repair is dependent on the extent and the depth of injury and the surviving chondrocytes and normal articular cartilage matrix. In injuries involving subchondral bone, there is no regeneration of the cartilage, but there is typically enlargement and progression of the lesion with associated pain.

The ultimate goal of treatment of these lesions is restoration of the cartilage, but in most cases this is not achieved.

Adult articular cartilage is not vascularized and, as stated above, lacks the capacity to regenerate itself after sustaining damage (Vangness, C. T., Jr. et al., Am. J. Orth. 33, No. 25S: 29, 2004). When cartilage is cut, without involvement of subchondral bone, the defect often will persist for the duration of the individual's life.

Treatment of articular cartilage defects may be either surgical or non-surgical. For example, several operative procedures are currently used to repair or remove damaged cartilage in order to prevent further destruction of the joint, decrease pain, and restore function. These include arthroscopic debridement and lavage, subchondral bone stimulating procedures, transplantation of chondrocytes or cartilage autografts and allografts and total knee arthroplasty. However, none of these produces regeneration of the native articular cartilage.

Thus, there is a desire for materials and methods for stimulating chondrogenesis.

BRIEF SUMMARY OF THE INVENTION

The invention provides, in an embodiment, an animal cartilage material in the form of a fluff. The fluff can be used for cartilage regeneration. Another embodiment of the invention provides a cartilage composition comprising non-demineralized particulate articular cartilage having large particle size, e.g., a size greater than 1,000 µm, such as about 6,000 µm. The cartilage composition can be used for cartilage regeneration. The invention also provides processes for preparing cartilage fluff and cartilage composition.

The invention also provides a method for regenerating cartilage comprises administering to a cartilage defect a therapeutically effective amount of a cartilage fluff or a cartilage composition. The method may also include administering one or more additional cartilage growth promoting factors. In some embodiments, the inventive cartilage fluff or cartilage composition may be press-fit into a defect without the use a matrix or without the use of a cover to contain the material.

The present invention provides one or more significant features. For example, the present invention provides a cartilage fluff or a cartilage composition with demonstrable chondrogenic activity. The cartilage fluff or cartilage composition according to the invention induces new cartilage formation in articular cartilage defects. The cartilage fluff advantageously packs the articular defect without the use of a matrix or vehicle, e.g., glycerol, collagen gel, etc., in combination with the fluff. The cartilage fluff and cartilage composition of the invention show complete or substantially complete regeneration of articular cartilage defects. When placed in a cartilage defect, the inventive cartilage fluff and cartilage composition produce new cartilage growth congruitous with the articular surface, e.g., in defects involving subchondral bone. Furthermore, new cartilage formation may be initiated rapidly. In embodiments, new cartilage formation begins within, a short period of time, e.g., two weeks, and complete, or substantially complete coverage of the defect may occur by about sixteen weeks.

Advantageously, embodiments of the present invention avoid the difficult process steps of extracting growth factors and proteoglycans and/or similar substances from cartilage with various chemical agents. Embodiments of the present invention produce effective cartilage fluff and cartilage compositions without deleteriously altering the growth factors and other substances present in the cartilage.

DETAILED DESCRIPTION OF THE INVENTION

In accordance with an embodiment, the present invention provides a cartilage fluff. The cartilage fluff can be used for stimulating chondrogenesis and/or producing cartilage regeneration. The cartilage fluff comprises articular cartilage material in the form of a cartilage fluff.

The present invention in an embodiment provides a cartilage fluff comprising an animal, e.g., human, cartilage material in the form of a fluff. The cartilage fluff comprises strands of animal cartilage material with the strands having an average length of about 200 µm or more, e.g., about 400 µm or more, about 600 µm or more, about 800 µm or more, about 1,000 µm or more, about 1,200 µm or more, about 1,400 µm or more, about 1,600 µm or more, about 1,800 lam or more, about 2,000 µm or more, about 2,200 µm or more, about 2,400 µm or more, about 2,600 µm or more, about 2,800 µm or more, to about 3,000 µm. Alternatively, or in addition, the average length can be about 2,900 µm or less, about 2,700 µm or less, about 2,500 µm or less, about 2,300 µm or less, about 2,100 µm or less, about 1,900 µm or less, about 1,700 µm or less, about 1,500 µm or less, about 1,300 µm or less, about 1,100 µm or less, about 900 µm or less, about 700 µm or less, about 500 µm or less, to about 300 µm or less. Preferably, the cartilage fluff has strands having an average length of about 1,000 µm to about 3,000 µm. More preferably, the cartilage fluff has strands having an average length from about 2,000 µm to about 3,000 µm.

Additionally, in embodiments of the invention, the cartilage fluff comprises strands of animal, e.g., human, cartilage material with the strands having an average width of about 30 µm or more, e.g., about 40 µm or more, about 50 µm or more, about 60 µm or more, about 80 µm or more, about 100 µm or more, about 120 µm or more. Alternatively, or in addition, the average width can be about 140 µm or less, about 130 µm or less, about 110 µm or less, about 90 µm or less, about 70 µm or less, about 50 µm or less, about 40 µm or less. Preferably, the cartilage fluff comprises strands of animal cartilage material with strands having an average width of about 40 µm to about 140 µm.

The cartilage fluff of the invention has one or more branches that are intertwined with one or more of the strands. The cartilage fluff comprises strands of animal, e.g., human, cartilage material with the strands having one or more branches of an average diameter up to about 50 µm. Preferably, the cartilage fluff comprises strands having one or more branches of an average diameter from about 5 µm or more, e.g., about 10 µm, about 20 µm, about 30 µm, about 40 µm, to about 50 µm. Alternatively, or in addition, the average diameter can be about 45 µm or less, about 35 µm or less, about 25 µm or less, about 15 µm or less, to about 5 µm. Preferably, the cartilage fluff comprises strands having one or more branches of an average diameter from about 5 µm to about 50 µm, more preferably, from about 10 µm to about 30 µm.

A significant property of the cartilage fluff is that it allows for the material to be packed efficiently into articular and bone defects without the need to mix it with a vehicle such as glycerol, collagen gel, etc. In an embodiment, the strands of cartilage in the cartilage fluff are intertwined, and thus form a matrix which supports itself. The matrix supports itself and will thus remain in the articular defect into which the cartilage fluff is placed. The physical configuration of the cartilage strands allow for release of cartilage regeneration factor from the strands, thus promoting efficient or rapid cartilage regeneration. Cartilage fluff encourages retention of clotted blood between the interwoven strands and promotes cartilage regeneration. Physically, in this respect, cartilage fluff resembles a cotton composition.

In another embodiment, the invention provides a cartilage composition comprising non-demineralized particulate cartilage having a particle size greater than 1000 µm. The particulate cartilage may have an average particle size from 1,100 µm or more, e.g., about 1,500 µm or more, about 2,000 µm or more, about 2,500 µm or more, about 3,000 µm or more, about 3,500 µm or more, about 4,000 µm or more, about 4,500 µm or more, about 5,000 µm or more, about 5,500 µm or more, to about 6,000 µm. Alternatively, or in addition, the average particle size can be about 5,800 µm or less, about 5,300 µm or less, about 4,800 µm or less, about 4,300 µm or less, about 3,800 µm or less, about 3,300 µm or less, about 2,800 µm or less, about 2,300 µm or less, about 1,800 µm or less, to about 1,300 µm or less. Preferably, the particulate cartilage has an average particle size from an average size from about 3,000 µm to about 6,000 µm, more preferably an average particle size from about 4,000 µm to about 6,000 µm, and even more preferably an average particle size from about 5,000 µm to about 6,000 µm.

Articular cartilage material may be obtained from any suitable source, e.g., articular surfaces of joints, such as from distal femurs, proximal tibias, acetabulums, heads of femurs, and/or heads of radiuses. The cartilage may be removed, for example, with a scalpel blade and preferably removed down to subchondral bone, without removing bone. The articular cartilage for use in the present invention may include articular hyaline cartilage, fibrocartilage, and mixtures thereof. The articular cartilage for use in the present invention may comprise allogeneic cartilage, xenogeneic cartilage, and mixtures thereof. Allogeneic cartilage may be obtained from a human cadaver. Xenogeneic cartilage may be obtained from a variety of animals. The articular cartilage for use in the present invention may comprise human cartilage. Preferably, the cartilage fluff allograft may be obtained from a human cadaver. Preferably, the cartilage fluff xenograft may be may be obtained from a variety of animals.

The articular cartilage is preferably non-demineralized. Preferably, the cartilage is not subjected to harsh chemical treatments, which can alter the inherent natural properties of cartilage material. For example, the cartilage is preferably not subjected to demineralization treatments such as treatment with hydrochloric acid, ethylene diamine, and/or other demineralization agents. The non-demineralized articular cartilage may optionally be subjected to microbiological testing or subjected to other testing protocols that do not deleteriously alter the cartilage.

Additionally, the articular cartilage is preferably not subjected to any physical treatment that may demineralize and/or alter the inherent natural properties of the cartilage. For example, the articular cartilage is preferably not subjected to elevated temperatures, e.g., temperatures greater than about 50° C., that may diminish the chondrogenic activity of the cartilage. The articular cartilage may be preserved, e.g., freeze-dried, frozen, cryo-preserved, and/or dried, after being removed from the joint. One preferred method of preserving articular cartilage is freeze-drying.

The cartilage material used in embodiments of the invention may be in the form of dry cartilage, freeze-dried cartilage, frozen cartilage, cryo-preserved cartilage, wet cartilage, or mixtures thereof. The cartilage for use in the present invention may include the same cartilage materials as previously disclosed. In an embodiment, the cartilage is freeze-dried. For example, pieces of cartilage obtained from the articular surface of one or more joints is washed in normal saline, preferably several changes of normal saline, blotted dry, and frozen rapidly, e.g., at 10° C./min or faster, in the vapor phase of liquid nitrogen (about −150° C.) or alternatively in the liquid phase of liquid nitrogen (about −196° C.). After being frozen, the cartilage is preferably rapidly placed directly on the shelves of a freeze-drying apparatus maintained at about −40° C. to about −50° C. (the condenser being cooled from about −70° C. to about −80° C.). A vacuum level of less than about 100 millitorr is preferably maintained in the freeze-drying chamber during the freeze-drying cycle. The freeze-drying cycle may last an average of about 5 days. During the initial 30-45 minutes of the cycle, the cartilage warms from the initial frozen temperature (e.g., about −150° C.) to the temperature of the freeze-drying chamber (e.g., about −40° C.), after which it is maintained at about −40° C. for the remainder of the cycle. Preferably, the moisture content of the cartilage is reduced to about 5% or less, preferably to about 4% or less, e.g., to about 3% to about 5%. Over drying is preferably avoided, as this may result in the irreversible alterations of collagen and proteoglycan structures. At the end of the freeze-drying cycle, the chamber is warmed to room temperature, the vacuum released and the freeze-dried cartilage is removed.

According to the invention, the articular cartilage may be ground or milled using any suitable grinding or milling apparatus. For example, any grinding or milling apparatus capable of grinding dry, hard, brittle material in seconds, such as turbo mills, disc mills, toothed disc mills, or jet mills are suitable for grinding or milling the cartilage.

Preferably, the grinding and milling are performed under conditions that preclude raising the temperature of the articular cartilage to a level that may diminish the chondrogenic activity of the cartilage material. For example, grinding is preferably performed without raising the temperature of the articular cartilage above about 50° C. In embodiments, grinding is preferably performed without raising the temperature of the cartilage above about 40° C. The temperature of the articular cartilage may be measured in any suitable manner. For example, thermocouples may be used to monitor the temperature of the cartilage directly, e.g., by measuring the temperature of the cartilage immediately after grinding, or indirectly, e.g., by measuring the temperature of the metal in the grinding mill. For example, continuous grinding in conventional grinding mills for 3-5 minutes can raise the temperature of the material to 70° C. or above. Continuous grinding or milling may be coupled with adequate cooling to keep the temperature at a desired level, e.g., at a temperature of 2° to 4° C. Operating a grinding mill intermittently may preclude an undesirable rise in temperature. In one embodiment, freeze-dried pieces of cartilage may be ground in a grinding mill operating intermittently for less than one minute, e.g., for about 20 to about 30 seconds, with intervals between grinding. Such intervals can be from about 30 to about 120 seconds.

Another method of preparing a cartilage fluff according to the present invention comprises freeze-drying cartilage to obtain a freeze-dried cartilage, grinding the freeze-dried cartilage to obtain a ground material comprising cartilage fluff, and separating the cartilage fluff from the ground material.

Preferably, after each grinding cycle, the cartilage may be sieved. The cartilage may be sieved through sieves of 850 µm and 1,000 µm size. Material remaining on the sieve exceeds the pore size of the sieve. Accordingly, the cartilage material may have an average length as previously disclosed. The cartilage fluff in accordance with an embodiment of the invention has a cohesive characteristic in that the fluff sticks to each other to form a network, e.g., a continuous network. This unique property allows for easy packing and treatment of an articular defect.

Another method of preparing a cartilage fluff according to the invention comprises freeze-drying articular cartilage, and milling the freeze-dried cartilage. For example, the milling may be carried out with a drill bit, core drill, or burr. The cartilage fluff according to the invention may be prepared by securing bone with cartilage in a milling and digitizing machine, and shaving the cartilage to obtain the cartilage fluff. Alternatively, the articular cartilage may be unattached to bone.

For example, the milling of the cartilage can be performed incrementally in an industrial type mill without over heating the cartilage. Overheating is prevented by employing milling cycles of 15-30 seconds. Alternatively, the chamber of the mill is cooled, e.g., by carbon dioxide, cryogenic gases or by placing the entire milling apparatus into a refrigerated chamber. Periodically, the milled material is placed into sieves and smaller particles are segregated by passing through the sieves with openings of 500 µm or less.

In accordance with another embodiment of the invention, the cartilage fluff may be prepared from freeze-dried cartilage by the use of a digitizing and milling machine, such as a Levil type. A freeze-dried cartilage block with or without bone is placed on the milling platform and the machine is activated. Preferably, after each milling cycle, small particles are sieved out of the cartilage being milled. The cartilage being milled may be placed into cryogenic gas vapor or other cold chamber to maintain it in a frozen state. The frozen cartilage may be replaced into the milling chamber and subjected to another cycle of milling. This process can be repeated several times as needed.

A method of preparing a particulate cartilage composition comprises freeze-drying cartilage to obtain a freeze-dried cartilage, grinding the freeze-dried cartilage to obtain a ground material comprising a particulate cartilage composition, and separating the particulate cartilage composition from the ground material. After each grinding cycle, the cartilage may be sieved. The cartilage may be sieved through sieves of 25 µm to 6,000 µm. Sieving may be used to separate cartilage into particle sizes of less than 1,100 µm and cartilage particle sizes of 1,100 µm to about 6,000 µm. Grinding may be repeated until any desired or preferred cartilage particle sizes are obtained.

The present invention further provides a method of regenerating articular cartilage in an animal, e.g., human, in need thereof comprising administering an effective amount of the cartilage fluff of the invention to a site of the animal where there is a need for regenerating articular cartilage. Therapeutically effective amounts of cartilage composition comprising an articular cartilage fluff of the invention may be administered at the site of a cartilage defect. The cartilage fluff may be implanted at the site, e.g., articular surface, and packed into the defect. In embodiments, the cartilage fluff may be packed without the use of a vehicle, which is advantageous for rapid regeneration of articular cartilage.

The present invention also provides a method of regenerating articular cartilage in an animal, e.g., human, in need thereof comprising administering an effective amount of a cartilage composition of the invention to a site of the animal where there is a need for regenerating articular cartilage. Therapeutically effective amounts of a cartilage composition comprising particulate cartilage having an average particle size of from 1,100 µm to about 6,000 µm may be administered at the site of a cartilage defect. The particulate cartilage composition may be implanted at the site, e.g., articular surface and packed into the defect. In embodiments, the cartilage composition may be packed into the defect with the use of an overlying cover.

The method may also include administering one or more additional cartilage growth promoting factors. Additives may be applied to the cartilage fluff or cartilage compositions in order to increase chondrocyte migration and proliferation. The cartilage fluff and cartilage compositions can support the addition of a variety of chondrogenic stimulating factors including, but not limited to growth factors (FGF-2, FGF-5, IGF-1, TGF-.beta., BMP-2, BMP-7, PDGF, VEGF), human allogenic or autologous chondrocytes, human allogenic or autologous bone marrow cells, stem cells, demineralized bone matrix, insulin, insulin-like growth factor-1, transforming growth factor-B, interleukin-1 receptor antagonist, hepatocyte growth factor, platelet-derived growth factor, Indian hedgehog and parathyroid hormone-related peptide or bioactive glue.

Without wishing to be bound to any theory, it is believed that cartilage fluff and cartilage compositions of the invention release cartilage growth factor(s) or other favorable substances that induce or enhance regeneration of articular cartilage. The three-dimensional shape of the fluff and the particles and multiple surfaces, as well as the inventive fluff sizes and particle sizes, enhance diffusion of the cartilage growth factor(s) or other substances from the fluff and the particles. Furthermore, the absence of harsh chemical treatments and avoidance of elevated temperatures during processing facilitates the production of fluff and particles having high chondrogenic activity.

The following example further illustrates the invention but, of course, should not be construed as in any way limiting its scope.

EXAMPLE

This example demonstrates the chondrogenic activity of the cartilage fluff in fully immunocompetent non-human primates. Full thickness cartilage defects measuring 10 mm×1 mm is created in the medial condyles of the animals. The defects are densely packed with the cartilage fluff according to the present invention and are compacted with a tamp. The animals are examined two, six, and sixteen weeks post transplantation and the joints are re-explored. Photographs taken at two, six, and sixteen weeks, respectively. Specimens are also taken and fixed in 10% formalin-Earle's balanced salt solutions. Paraffin sections are cut and stained with homotoxylin and eosin, PAS, Romanowski-Giemsa and Safranin-O stains.

At two weeks post transplantation, granulation tissue is present in the center of the defect and new cartilage is present at the edge of the defect. At six weeks post transplantation, new cartilage is formed from the edges of the defect and granulation tissue is no longer present and the cartilage composition is covered with a translucent membrane in the center of the defect. At six weeks, the hyaline cartilage shows normal morphology. At sixteen weeks post transplantation, the defect is completely healed and covered with congruous normal appearing cartilage. At sixteen weeks, normal appearing hyaline cartilage is formed. The control, where the defect is left untreated, shows no evidence of healing; the defect becomes larger due to additional fragmentation of the cartilage.

All references, including publications, patent applications, and patents, cited hen are hereby incorporated by reference to the same extent as if each reference were individually and specifically indicated to be incorporated by reference and were set forth in its entirety herein.

The use of the terms "a" and "an" and "the" and similar referents in the context describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventor for carrying out the invention. Of course, variations of those preferred embodiments will become apparent to those of ordinary skill in the art upon reading the foregoing description. The inventor expects skilled artisans to employ such variations as appropriate, and the inventor intends for the invention to be practiced otherwise than as specifically described herein. Accordingly, this invention includes all modification equivalents of the subject matter recited in the claims appended hereto as permitted by applicable law. Moreover, any combination of the-above-described elements in all possible variations thereof is encompassed by the invention unless otherwise indicated herein or otherwise clearly contradicted by context.

What is claimed is:

1. A treatment method of regenerating articular cartilage comprising: administering a therapeutically effective amount of a cartilage fluff composition at the site of a cartilage defect, the fluff having a size 1,100 μm to 6,000 μm made of a plurality of intertwined branched strands in the form of a continuous network of cartilage fluff for packing; and packing the cartilage fluff into the site, wherein the fluff is directly packed with or without the use of a vehicle.

2. The treatment method of claim 1 wherein the fluff is directly packed without the use of a vehicle.

3. The treatment method of claim 1 further comprises the step of: using an overlying cover.

4. The treatment method of claim 1 further comprises the step of: administering one or more additional growth promoting factors or additives applied to the cartilage fluff to increase chondrocyte migration and proliferation.

5. The treatment method of claim 4 wherein the growth factors include one or more of: FGF-2, FGF-5, IGF-1, TGF-13, BMP-2, BMP-7, PDGF, VEGF, human allogenic or autologous chondrocytes, human allogenic or autologous bone marrow cells, stem cells, demineralized bone matrix, insulin, insulin-like growth factor-I, transforming growth factor-B, interleukin-1 receptor antagonist, hepatocyte growth factor, platelet-derived growth factor, Indian hedgehog or parathyroid hormone-related peptide.

6. The treatment method of claim 1 wherein the cartilage fluff releases cartilage growth factors that induce or enhance regeneration of articular cartilage.

\* \* \* \* \*